US006836332B2

(12) United States Patent  
Mosley et al.

(10) Patent No.: US 6,836,332 B2
(45) Date of Patent: Dec. 28, 2004

(54) INSTRUMENT AND METHOD FOR TESTING FLUID CHARACTERISTICS

(75) Inventors: R. Matthew Mosley, Spartanburg, SC (US); Douglas J. Paul, Seneca, SC (US); John N. Pike, Pleasantville, NY (US)

(73) Assignee: Tennessee Scientific, Inc., Greenville, SC (US)

( * ) Notice: Subject to any disclaimer, the term of this patent is extended or adjusted under 35 U.S.C. 154(b) by 1 day.

(21) Appl. No.: 09/964,144

(22) Filed: Sep. 25, 2001

(65) Prior Publication Data

US 2003/0058450 A1 Mar. 27, 2003

(51) Int. Cl.$^7$ ............................................. G01N 21/00
(52) U.S. Cl. ...................................... 356/436; 356/73
(58) Field of Search ............................... 356/436–440, 356/337–343, 73

(56) References Cited

U.S. PATENT DOCUMENTS

| | | | |
|---|---|---|---|
| 5,489,977 A | * | 2/1996 | Winslow et al. ............... 356/73 |
| 6,118,531 A | * | 9/2000 | Hertel et al. ................. 356/336 |
| 6,519,033 B1 | | 2/2003 | Quist et al. .................. 356/337 |
| 6,590,652 B2 | | 7/2003 | Quist et al. .................. 356/338 |

OTHER PUBLICATIONS

"Light Scattering Technique Detects Pathogenic Aerosols", Jun. 2003, Photonics Spectra p21, reprinted from Optics letters Apr. 15, 2003, pp 589–591.

Peter C. Hauser and David W. Chiang, "A Photometric Detector Based on a Blue Light–Emitting Diode," Jan. 26, 1993, Talanta, vol. 40 No. 8, pp. 1193–1200, Copyright © 1993 Pergamon Press Ltd.

Peter C. Hauser, Thusitha W. T. Rupasinghe, and Norman E. Cates, "A Multi–Wavelength Photometer Based on Light Emitting Diodes," Oct. 27, 1994, Talanta, vol. 42 No. 4, pp. 605–612, Copyright © 1995 Elsevier Science Ltd.

R. James Berry, Jay E. Harris, and Ronald R. Williams, "Light–Emitting Diodes as Sensors for Colorimetric Analyses," Apr. 17, 1997, Applied Spectroscopy, vol. 51, No. 10, pp. 1521–1524, Copyright © 1997 Society for Applied Spectroscopy.

Raimund Barden and Rainer Peters, "CPM Enables Sizing of SubMicron Particles," Mar. 2002, Laser Focus World, p. 99 et seq.

* cited by examiner

Primary Examiner—Frank G. Font
Assistant Examiner—Amanda Merlino
(74) Attorney, Agent, or Firm—McCarter & English, LLP

(57) ABSTRACT

An instrument for testing fluid characteristics has a vial and a housing. The vial defines a chamber for receiving a sample of the fluid and has a cap for sealing the fluid therein. The housing defines a recess for receiving the vial. Multiple light emitting diodes and photovoltaic detectors are arranged on multiple meridional planes within the housing. The meridional planes each intersect approximately at a central axis of the chamber when the vial is placed within the recess. Modulation of the light emitting diodes and tuned processing electronics allow for simultaneous evaluation of sample characteristics such as spectral transmittance, turbidity and fluorescence. The user selects particular tests via a keypad and a display indicates the results of the chosen analysis.

62 Claims, 8 Drawing Sheets

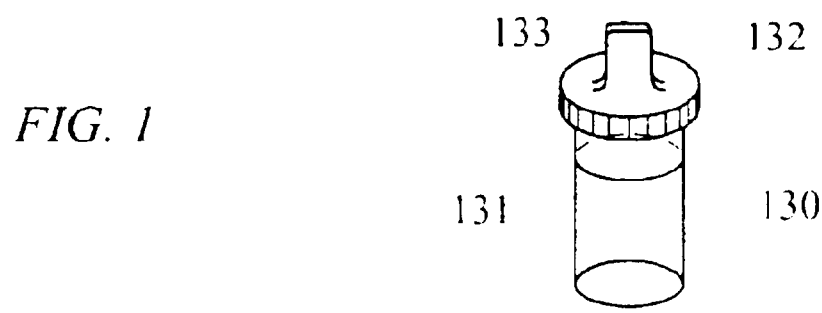
FIG. 1
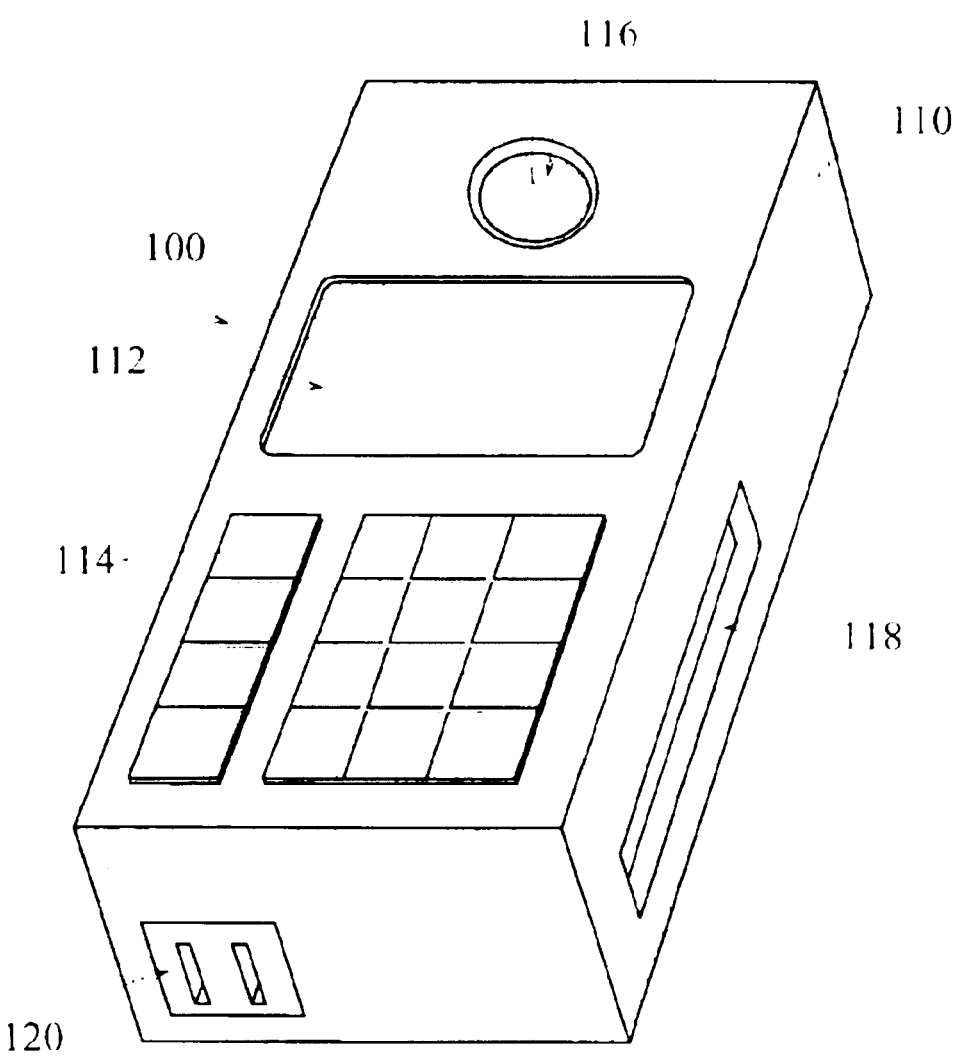

INSTRUMENT AND METHOD FOR TESTING FLUID CHARACTERISTICS

BACKGROUND OF THE INVENTION

1. Field of the Invention

The subject invention relates to instruments for measuring the characteristics of fluids, and more particularly, to an improved instrument and method for testing the color, turbidity and/or fluorescence of fluids such as water mixed with a reactant.

2. Background of the Related Art

Water quality monitoring at all levels of production and usage is rapidly becoming a global necessity as sources of fresh potable water become taxed by increasing populations. Even low levels of foreign matter or contaminants can pose significant health and safety risks when undetected. As a result, fast and accurate water testing results are required of an ever-expanding source of test samples. Consequently, there is a growing need for rugged portable instruments and methods for monitoring water quality as the treatment and usage of water expands.

Typically, the testing of water quality has involved the addition of a specified reagent to a fluid sample. Conventionally, a reactant of known concentration is mixed with a water sample which contains a reactant of an unknown concentration. Alternatively, the known reactant is continually added until a sample property change indicates the endpoint of the reaction. In either case, the reagent reacts with the contaminant to create a reaction proportionate to the concentration of the contaminant. Often, a color indicator is included so that a color change occurs, or the color change is inherent to the chemical reaction. Thus, subsequent to the addition of the reagent, visual inspection against a printed color chart can determine the absence or level of an associated contaminant. Such purely visual comparisons are inherently subjective, and therefore unreliable for sensitive measurements. Generally, a skilled technician is required to determine the degree of the reaction and interpret the results. Alternatively, a colorimeter or photometer can consistently measure the degree of reaction (e.g., the depth of color or the spectral transmission) and, hence, the concentration of the contaminant. However, traditional calorimeters and photometers are not practical for field use and provide only color related data.

When the reaction product is a fine-particle precipitate, the sample can be measured by optical turbidimetric methods, i.e. scattering. A high concentration of precipitate as a result of a high concentration of the contaminant creates increased scattering. Therefore, the level of turbidity corresponds to the level of contaminant concentration. Alternatively, the presence or absence of a level of turbidity from a source in a natural fluid sample may be a critical indicator of the quality of such a fluid sample.

An additional technique is to add a reagent including a fluorescent marker. The reaction with the contaminant may either enable or quench the fluorescent moiety. For example, the marker rhodamine will fluoresce in the red when excited by blue light. Thus, transmitting blue light through the sample will generate a red fluorescence proportionate to the level of contaminant. Accordingly, determining the change in the level of fluorescence will indicate the concentration of the contaminant. Additionally, if the blue exciting light is repetitively pulsed and the fluorescence intensity is measured at a particular time after each pulse, the time-decay rate of the fluorescence can provide further information on the chemical nature of the contaminant.

In view of the above, several systems have been developed to ascertain the color, turbidity or fluorescence of a liquid sample. A traditional calorimeter includes a broadband light source. Filters are moved in and out of the optical path to provide different wavelengths. The filters may be moved manually or by motors. A lightpipe or lens system may collect and direct the light to a point on the object to be tested. At such points, the light reflects off opaque objects and passes through translucent objects to receivers. The receivers, usually photodiodes, convert the light signal into an electrical signal for processing. To prevent erroneous readings, the receiver must be isolated from ambient light. To control the environment, the conventional colorimeter is usually utilized exclusively in a laboratory.

For example, U.S. Pat. No. 5,137,364 to McCarthy discloses an optical spectral analysis device having light emitting diodes (hereinafter "LEDs") and receivers mounted on the same substrate. Thus, only reflected light is analyzed. U.S. Pat. No. 5,229,841 to Taranowski et al. shows using a plurality of different colored LEDs which are run according to timing pulses. In synchronism with the LED timing pulses, the outputs of the photodiodes are sampled, and thus each output is indicative of an individual colored LED's signal. U.S. Pat. No. 6,094,272 to Okamoto discloses receiving a sum total of reflected light and comparing the summed value to a value associated with a reference target. The resulting comparison value is displayed in numerical form to indicate a match degree between the tested item and the reference item. U.S. Pat. No. 6,157,454 to Wagner et al. discloses a miniature calorimeter. The miniature colorimeter includes a body having a light pipe for transmitting reflected light to a light sensor, three different primary colored light sources, a display panel and a measure button. In operation, the miniature colorimeter generates three color data points representing the reflectance of the target measured at the wavelengths of the three primary colors. A microprocessor analyzes the three data points and displays the results in various commonly known formats. Further, several patents are directed specifically to water testing methods and devices. U.S. Pat. No. 5,618,495 to Mount et al. automates the process of determining when the endpoint of the reagent reaction is reached with the use of a computer in communication with a colorimeter and other devices. U.S. Pat. No. 5,691,701 to Wohlstein et al. uses the voltages generated by photosensors to produce a ratio which indicates the condition of engine oil. If the test fluid is outside a preset acceptable limit, an alarm indicating the same is triggered.

A multitude of patents are directed to particular aspects of photoelectrically sensing the color of an object. For example, U.S. Pat. No. 5,303,037 to Taranowski discloses a color sensor illumination source which generates a white light evenly composed of red light, green light and blue light directed at the same angle. The importance of a balanced source is to yield relatively balanced color output readings. U.S. Pat. No. 5,471,052 to Ryczek shows a secondary photosensitive element which receives the light directly from the light source. As a result, the signal from the secondary photosensitive element is used to create a closed loop feedback signal to regulate the light source power output.

Additional patents have recognized that certain materials display different colors depending upon the angle of observation. In particular, U.S. Pat. No. 5,592,294 to Ota et al. recognizes the need to accurately determine the angle of observation in order to render reproducible results. To solve this problem, Ota et al. incorporated an angle detector which controls an adjustment mechanism in order to set the desired angle of observation repeatably.

U.S. Pat. No. 5,083,868 to Anderson discloses the need for a portable colorimeter. The colorimeter is enclosed in a housing for receiving a sample. When a vial is placed in the sample compartment, a cap member is positioned in grooves to prevent interference from external light. U.S. Pat. No. 5,872,361 to Paoli et al. discloses a portable turbidimeter having a non-imaging optical concentrator between a sample cell and an optical detector. A cover is utilized to reduce the effect of ambient light on the readings. U.S. Pat. No. 5,604,590 to Cooper et al. discloses a nephelometer instrument for measuring very high water turbidities, such as 10,000 NTUs. The nephelometer instrument has one light source and four detectors. The detectors receive back scatter, forward scatter, 90° scatter and transmitted light.

Still further, several patents are directed to devices for only determining the light penetrability of liquids. U.S. Pat. No. 5,696,592 to Kuan teaches immersing a light guide and a liquid-tight photosensor in a liquid to be measured. When a light source illuminates the light guide, the photosensor generates a signal indicative of the penetrability of light for the test liquid. U.S. Pat. No. 6,055,052 to Lilienfeld is directed to a system for monitoring airborne particulates. Lilienfeld appreciates the need for a portable instrument which can determine ambient air quality in real time at remote locations. Each of the U.S. patents described above are incorporated herein by reference.

Despite the teachings of the above-mentioned patents, there are various problems associated with the systems and methods of the prior art as known in the field of water testing. Many systems require the time-consuming process of acquiring a sample and sending the sample to a laboratory for analysis. Alternatively, on-site analysis is often subjected to inconsistent results due to human error. Further, devices of the prior art, particularly those designed for portable field use, yield only limited results. In the past, providing a device that could consistently and accurately indicate contaminant levels was far less than economic regardless of the location. There is a need, therefore, for an improved water testing instrument and method which permits efficient and accurate readings of at least one, and preferably a plurality of parameters for a variety of applications and operating conditions.

SUMMARY OF THE INVENTION

The present invention is directed to a method and device for optically measuring qualities of a substance in ambient light, wherein the device includes a translucent wall defining a sample chamber and an axis. The translucent wall contains the substance to be measured. A radiation source, such as an LED or other light source, is mounted adjacent to the sample chamber and emits a modulated beam of radiation distinguishable from the ambient light because the radiation is modulated. After passage through the sample chamber, the radiation is received by a detector angularly spaced about the axis of the sample chamber relative to the radiation source. The detector generates a modulated output signal indicative of the intensity of the radiation of the beam impinging thereon. A controller activates the radiation source and the detector and processes the modulated output signal for show on a display.

The present invention is also directed to an instrument and method for measuring characteristics of a substance, wherein the instrument includes a sample chamber for receiving therein a sample of the substance. A signal generator has a radiation source mounted adjacent to the sample chamber. The radiation source emits a beam of radiation through the sample chamber onto a detector of the signal generator angularly spaced about the axis of the sample chamber relative to the radiation source. The detector receives the beam of radiation after passage through the sample chamber and substance to be measured therein. Upon receiving the radiation, the detector generates an output signal indicative of the intensity of the radiation impinging thereon. A memory stores reference measurement data based upon a plurality of different reference samples, wherein each reference sample has a different concentration of an impurity. A controller in communication with the memory is operative to receive a signal from the signal generator based upon a sample within the sample chamber having an unknown concentration of an impurity. The controller automatically compares the signal to the reference measurements to determine a concentration of the impurity in the sample and generate an output signal indicative of the concentration.

The present invention is also directed to a method and device for analyzing color and scattering of an elongated sample, such as a water sample contained in a vial, wherein the elongated sample defines an axis. The device includes a first channel defining a first meridional plane having a first radiation source mounted adjacent to the sample. The first radiation source emits a first beam of radiation through the sample onto a first sensor angularly spaced about the axis of the sample relative to the first radiation source. The first sensor generates a first output signal indicative of the intensity of radiation impinging thereon. A second channel defines a second meridional plane and includes thereon a second radiation source mounted adjacent to the sample. The second radiation source also emits a beam of radiation through the sample onto a second sensor angularly spaced about the axis of the sample relative to the second radiation source for generating a second output signal. Electronics activate each of the channels and process the signals generated thereby. Preferably, the channels are about 45° apart to allow for color, transmission and 45° turbidity measurements.

One advantage of the instrument and method of the present invention, is that they employ light sources which are modulated, and therefore the signals generated thereby can be isolated. As a result, the instrument and method are capable of functioning in ambient light. Further, multivariate analysis can be conducted simultaneously to gather data faster than with traditional mechanisms.

Still another advantage of the subject invention is the simplified arrangement of stationary components which perform a multitude of measurements. As a result, the reliability is improved and production costs are reduced.

These and other unique features and advantages of the instrument and method disclosed herein will become more readily apparent from the following description, the accompanying drawings and the appended claims.

BRIEF DESCRIPTION OF THE DRAWINGS

So that those having ordinary skill in the art to which the disclosed instrument and method appertains will more readily understand how to make and use the same, reference may be had to the drawings wherein:

FIG. 1 illustrates a perspective view of an instrument for measuring optical transmission, turbidity and fluorescence of a fluid sample constructed in accordance with subject disclosure;

FIG. 6b is a cross-sectional view taken along line A—A of FIG. 6a;

FIG. 7b is a cross-sectional view of the base of the sample vial of FIG. 7a; and FIG. 7c is a bottom plan view of the base of the sample vial of FIG. 7a.

DETAILED DESCRIPTION OF THE PREFERRED EMBODIMENTS

Figure 2A:
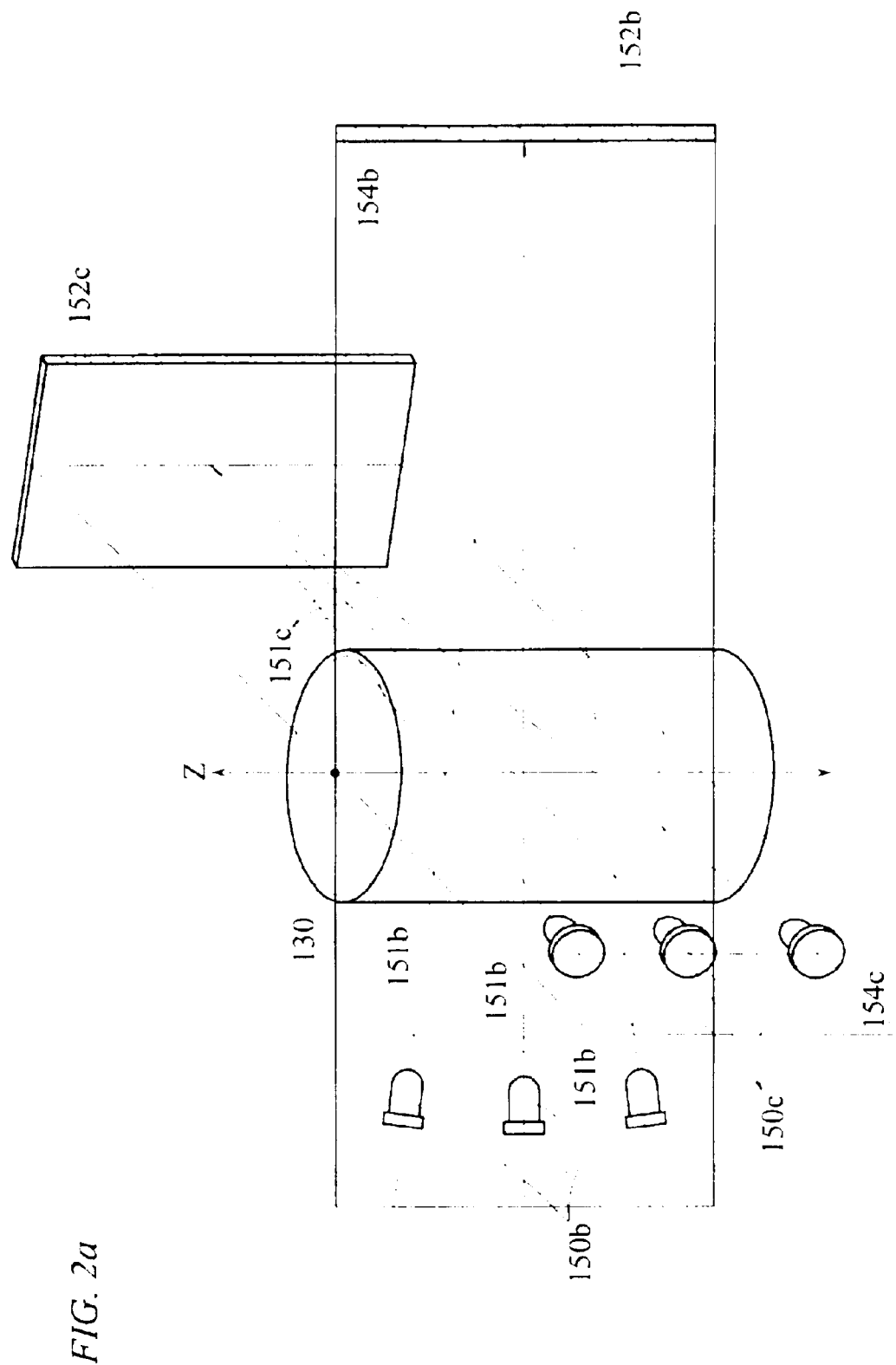
FIG. 2a is a partial schematic, perspective view of the optics of an instrument constructed in accordance with a preferred embodiment of the subject disclosure, wherein only two of three envisioned meridional planes are shown for simplicity.

The present invention overcomes many of the prior art problems associated with water testing devices and methods. The advantages, and other features of the instrument and method disclosed herein, will become more readily apparent to those having ordinary skill in the art from the following detailed description of certain preferred embodiments taken in conjunction with the drawings which set forth representative embodiments of the present invention, and wherein like reference numerals identify similar structural elements.

Figure 3:
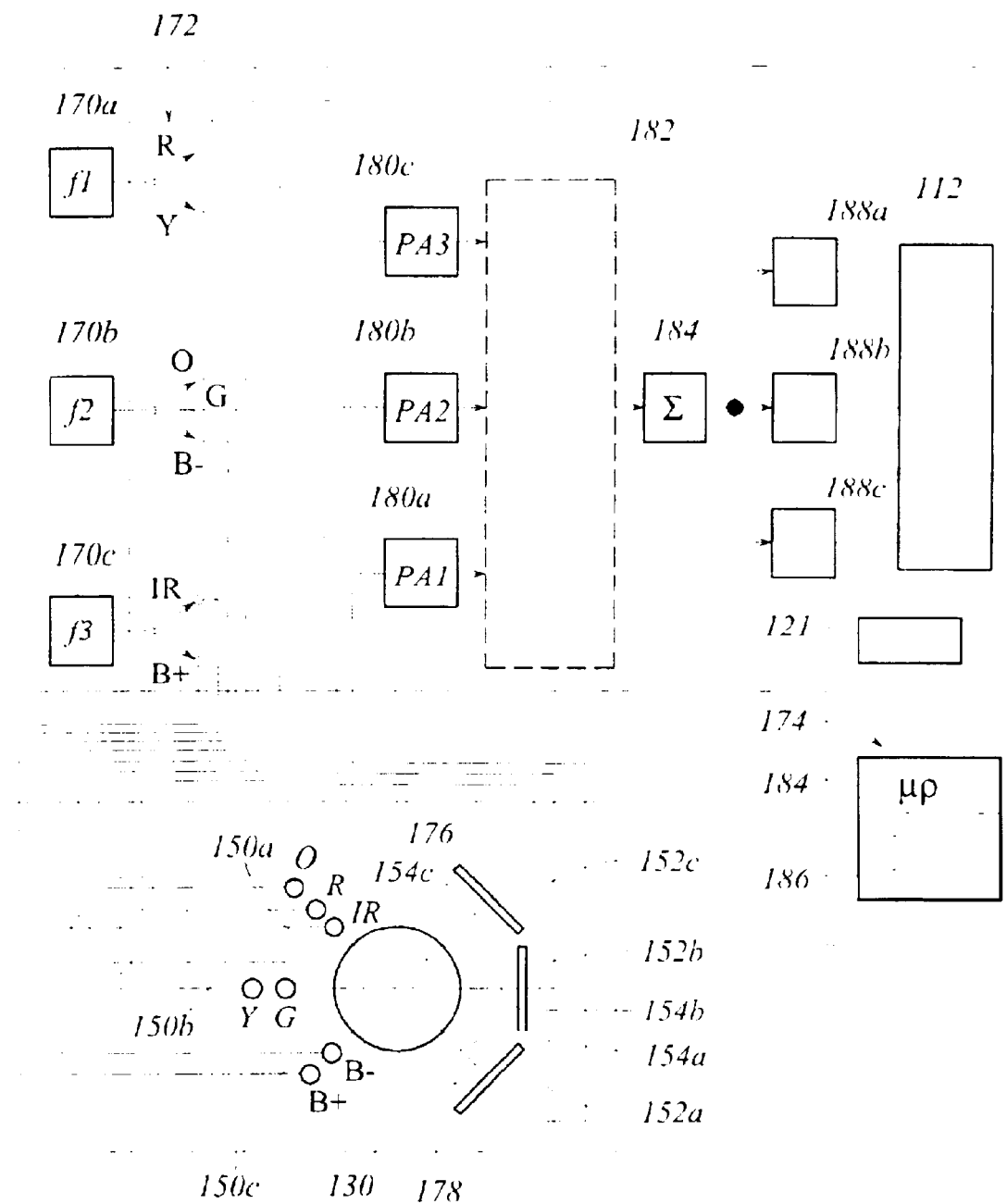
FIG. 3 is a schematic view of the optics and electronics of an instrument constructed in accordance with a preferred embodiment of the subject disclosure.

Referring to FIG. 1, a multi-axis photometric sensing instrument 100 includes a housing 110 for protecting and aligning optical components mounted therein, a display 112 for indicating the results of a plurality of measurements to a user, and a keypad 114 for receiving input from a user. The housing 110 defines a recess 116 for receiving therein an elongated sample vial 130 defining a chamber therein for receiving a sample to be tested. As described further below, the recess 116 properly aligns the sample vial 130 in the optical path for analysis. A port 118 for communicating with a computer (not shown) and a socket 120 for charging an internal power cell 121 (as seen in FIG. 3) are also integrated within the housing 110. Preferably, the port 118 is a serial, USB, IEEE1394 port or the like as is known to those of ordinary skill in the pertinent art.

Preferably, the instrument 100 is watertight to increase its ruggedness. The optics and electronics, which in the currently preferred embodiment are LEDs and photovoltaic detectors (hereinafter "PVDs"), are fixed within the housing 110. It is envisioned that a multitude of optical and electrical components may be used to fulfill the performance requirements of the instrument. For example, without limitation, semiconductor lasers may replace the LEDs and photoFETs (photosensitive field-effect transistors) or avalanche photodiodes may replace the PVDs. It is envisioned that any useful combination of analog and digital signal-processing electronic components may be used as the electrical components. Reducing the number of moving parts provides for increased reliability. As described in further detail below, the multi-axis, multi-source and multi-detector instrument 100 is selectively operated by electrical switching to perform a plurality of tests.

Preferably, the sample vial 130 is a thin-walled, visually transparent or translucent, non-scattering scintillation tube in the form of a wide-mouth, capped bottle. In a preferred embodiment, the sample vial 130 is in the form of a clear glass or plastic cylinder having a height of about 2 inches and a diameter of about 1 inch. As a result, the sample vial 130 will refract light passing therethrough. The medium within the sample vial 130 will also interact with light passing through the sample vial. It is also envisioned that the sample vial 130 can be square, rectangular, oblong or a multitude of other shapes as will be appreciated by those of ordinary skill in the pertinent art upon review of the teachings herein.

The sample vial 130 has a tabbed, screw-on plastic cap 132. The cap 132 is preferably provided with a tab portion 133 for labeling, tightening leverage when wet, and ease of handling. In one embodiment, the sample vial 130 is disposable to avoid cross-contamination from previous tests. Preferably, the sample vial 130 has a fill line 131 for indicating the required amount of sample. As may be recognized by those of ordinary skill in the pertinent art based on the teachings herein, the dimensions, materials of construction, and shape of the sample vial 130 or other structures defining the sample chamber disclosed herein are only exemplary, and may be changed as desired depending upon the particular application of the instrument or otherwise as desired.

In operation, the sample vial 130 is filled with the test fluid and placed within the recess 116 of the instrument 100. For example, the test fluid may be a water sample taken from the output of a drinking water supply. In a preferred embodiment, the sample vial 130 acts both as a sample holder and an optically refractive element necessary to the instrument's functioning. In the illustrated embodiment, all other hardware and software resides permanently in the remainder of the housing 110, and specific instructions for any chemical/turbidimetric tests are entered through the keypad 114 of the housing 110. The user selects via the keypad 114 an appropriate test such as, without limitation, color, turbidity and/or fluorescence, as described in further detail below. The instrument 100 analyzes the test fluid and the display 112 indicates the results of the test.

Now referring to FIG. 2a, only meridional planes 154b and 154c are shown for simplicity. The sample vial 130 is located between multiple LEDs 150 and PVDs 152 when placed within the recess 116. In one embodiment, nine LEDs 150 are arranged so that the principle rays 151 emitting therefrom define three meridional planes 154 passing through a central axis "z" of the sample vial 130 and converging at the central points of their corresponding PVDs 152. The selection and arrangement of the LEDs 150 and PVDs 152 creates a plurality of defined meridional planes 154a–c about the sample chamber's axis z. The LEDs 150 emit in a forward direction, but there is no need to further control the cone angle of the emission, other than the refractive focussing performed by the sample vial 130. Preferably, the LEDs 150 are relatively small view-angle LEDs. As shown, each of the LEDs 150 and PVDs 152 lie on defined, fixed axes, and the meridional planes 154a–c pass through axis z of the preferably cylindrical sample vial 130. Any angle effects are automatically taken into account by zeroing with a pure water sample, as described further below. In a currently preferred embodiment of the present invention, the three defined meridional planes 154a–c (or "channels") provide a total of nine different wavelength bands distributed over the near ultraviolet, visible and near infra-red (hereinafter "NIR") range for liquid optical absorption. The resulting sensitivity and precision of photometric transmission measurement exceeds that of the human eye, and extends the usefulness of the chemical tests beyond that of classical visual color determination. In one embodiment, the LEDs are selected with approximately 5 mm diameters and high brightness. The color of the light may be, without limitation, blue (430 nm peak emission wavelength), green (565 nm), red (660 nm), near IR (880 or 940 nm) and white. Preferably, the white LED is part number CMD333UWC available from Chicago Miniature Lamp. It is envisioned that other selections of LEDs, PVDs, and other light sources and detectors, including the wavelengths and positions of such light sources and detectors, would be obvious to one skilled in the art upon review of the subject disclosure.

Preferably, each LED's emission cone, the refractive power of the sample vial 130, and the width of each PVD 152, are selected in combination to capture the full cone of light within the corresponding PVD. The circular cone of light emitted by each LED 150 is distorted into an oblong shape by passing through the sample vial 130. Hence, the rectangular shapes of the PVDs are needed to catch all of the light. In a preferred embodiment, each LED 150 is a high-brightness T-1¾ LED located approximately 5 mm from the sample vial 130. Each LED emits into a forward cone which preferably has a view-angle of less than about 30°, with emission roughly uniformly distributed within this cone of light. Each PVD 152 has an approximately 20×40 mm rectangular active area. A suitable PVD is available from Radio Shack under part number #276-124A. Each PVD is placed approximately 19 mm from the sample vial 130 to collect the forward cone of light emitted by the corresponding LEDs. In another embodiment, a PVD of approximately 20×20 mm may be used with a small cylindrical lens (axis horizontal, not shown) placed in front of each LED 150 in the 5 mm space between the LED and the sample vial 130. The cylindrical lens condenses the vertical beam spread to fit on a 20 mm high PVD or other sensor. The PVDs 152 are used in the photovoltaic mode to assure linearity of response to input signals, no dark current, and minimal sensitivity to the operating temperature of the instrument 100. As may be recognized by those of ordinary skill in the pertinent art based upon the teachings herein, the dimensions and angles herein are only exemplary and may be changed as desired or otherwise required.

Preferably, the optical system is simple to construct, and requires no rigid tolerancing, as shown. To facilitate lightweight construction and automatic alignment of the LEDs 150 in each meridional plane 154, a piece of metal or plastic (not shown) may be machined or molded to secure the LEDs in place. In another embodiment, clear glass or like transparent or translucent covers (not shown) are epoxied or otherwise secured over the LEDs 150 and/or PVDs 152 to prevent water and dirt buildup. In still another embodiment, a Wratten blue-pass filter (not shown) is cemented over the blue-emitting LEDs in one of the meridional planes to not only aid cleanliness, but to increase the signal-to-noise ratio during measurements. As described further herein, the instrument 100 includes a microcontroller 174 (as best seen in FIG. 3) programmed in a manner known to those of ordinary skill in the pertinent art to control the various switching regimes. Consequently, the only moving part in the instrument 100 is preferably the hand-inserted sample vial 130.

In another embodiment, four PVDs 152 can be arranged in an octagonal arrangement (not shown). In the octagonal arrangement, four LED channels and four PVDs 152 allow twelve different LEDs 150 to be used simultaneously for photometric, transmission and turbidimetric or colorimetric purposes. It is envisioned that small interference filters (not shown) in front of some of the LEDs can be used to sharpen the spectroscopy, if desired. Preferably, each of the four PVDs 152 is approximately 20×40 mm; however, as may be recognized by those of ordinary skill in the pertinent art based upon the teachings herein, these dimensions are only exemplary and may be changed as desired or otherwise as required.

Figure 2B:
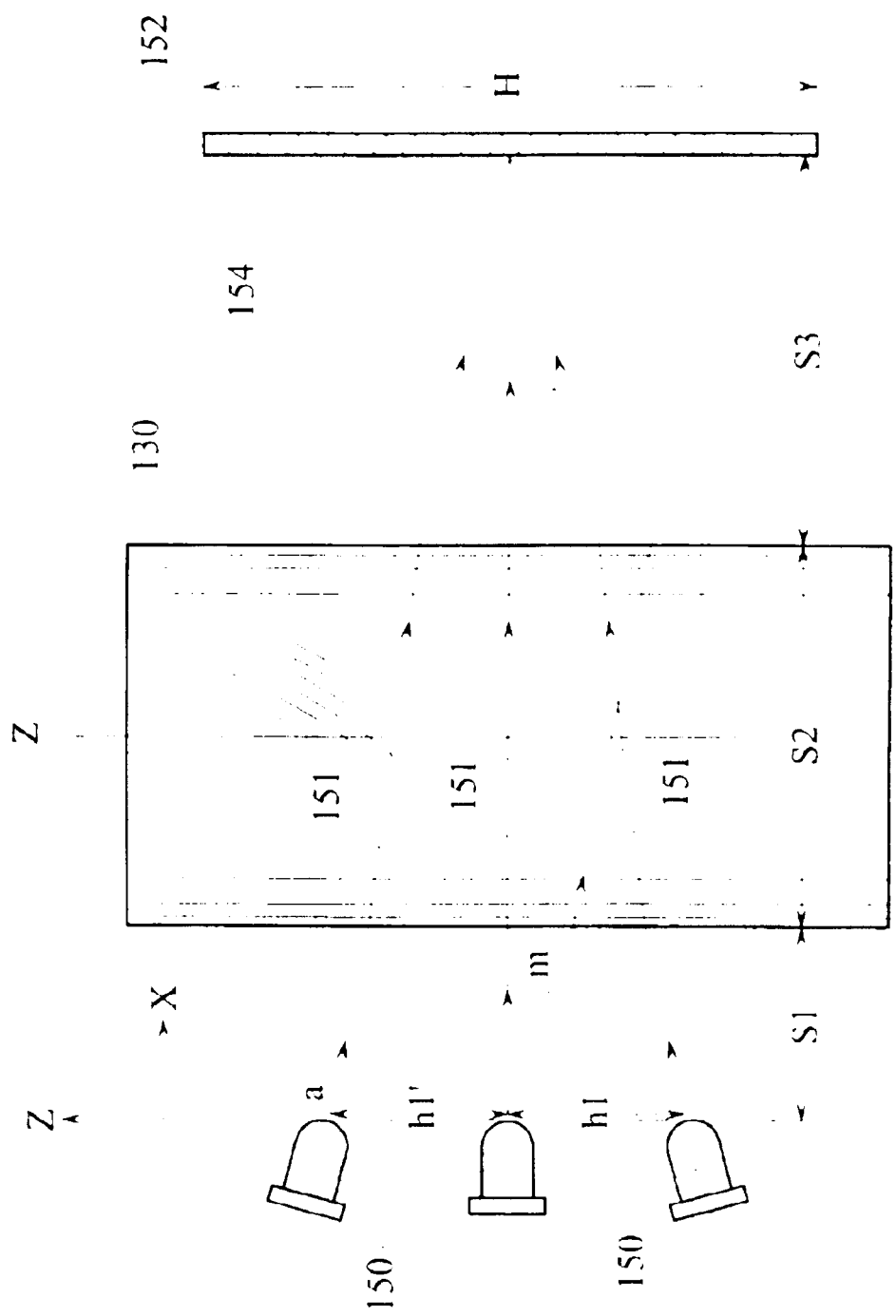
FIG. 2b is a partial schematic, side view of one meridional plane showing the principle rays of three LEDs of an instrument constructed in accordance with a preferred embodiment of the subject disclosure.
Figure 2C:
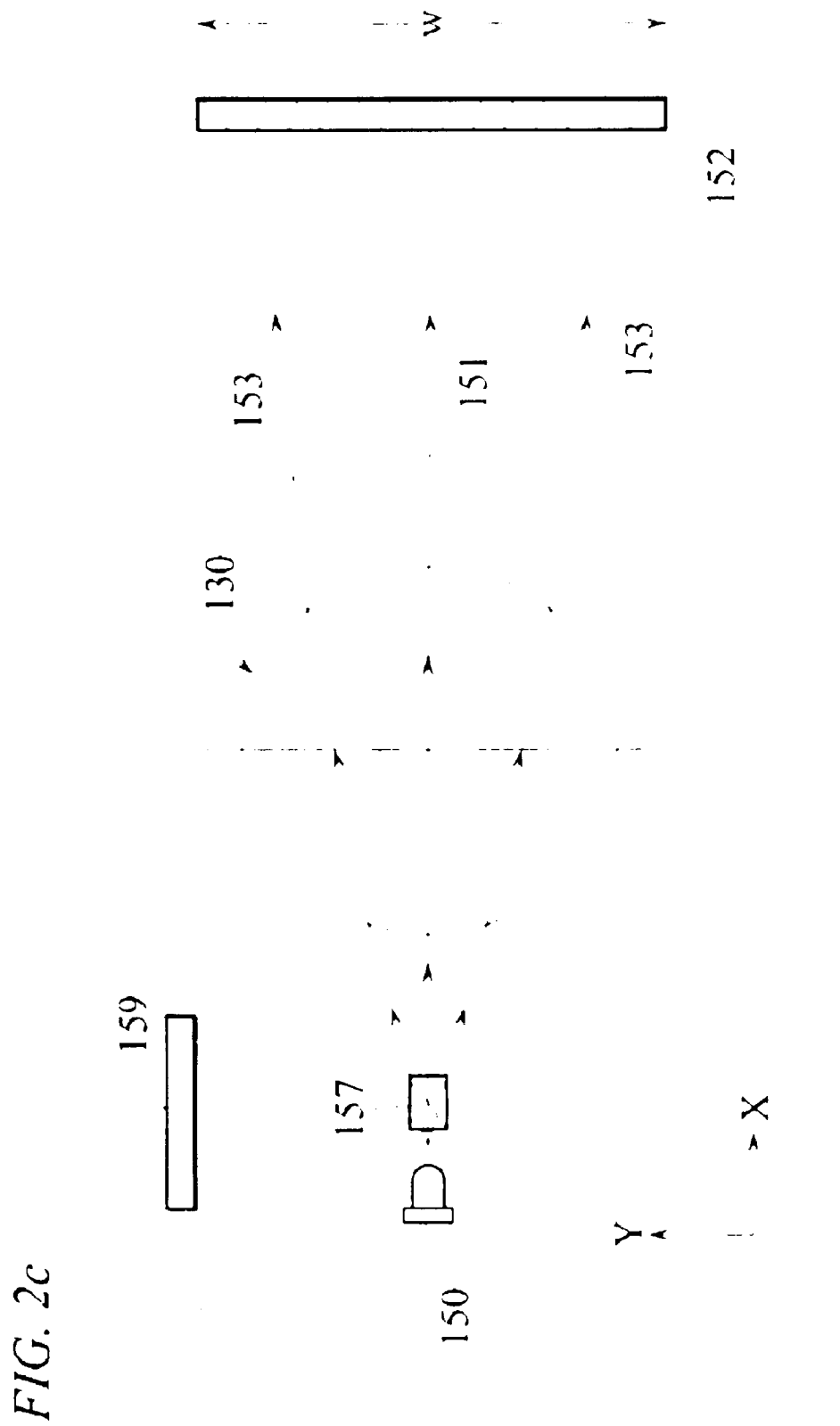
FIG. 2c is a partial schematic, top view of one meridional plane showing the principle ray and outermost rays of one LED of an instrument constructed in accordance with a preferred embodiment of the subject disclosure.

Referring now to FIGS. 2b and 2c, only one meridional plane 154 of the sensor is shown for simplicity. As shown, the meridional plane 154 lies in the plane defined by the axes x and z of a rectangular coordinate system. It will be appreciated by those skilled in the art that the meridional plane 154 shown represents the configuration of any of meridional planes 154a–c and that axis z may be in any spatial direction. For the preferred embodiment's capped sample vial 130, the most sensible direction to define axis z is approximately vertically upwards. For other embodiments, such as the sample vial or chamber defined by a quartz pipe or other transparent or translucent conduit for receiving flowing fluids therethrough and described further below, there are no practical restrictions on the length and orientation of axis z. In another embodiment shown in FIG. 2c, a plain-glass beam-splitter 157 and small reference photocell 159, are positioned so as to provide continuous monitoring of LED output power and feedback to correct for LED variations, if such referencing is needed or desired.

As shown in FIG. 2b, the LEDs 150 are located at a distance "s1" in the x axis from the left glass wall of the sample vial 130 in the drawing, and are spaced some minimal distance "h1" in the z axis from each other. The principal ray 151 of each LED in the meridional plane 154 intersects the central portion of the respective PVD 152 along the z axis. The PVDs 152 are oriented approximately perpendicular to the central axis of the meridional plane 154, and are spaced a distance "s3" in the x axis from the sample vial 130 in the drawing. As shown in FIGS. 2b and 2c, the exemplary PVD 152 defines a height "H" and width "W" and receives light from any or all of the respective meridional plane's LEDs, sequentially or simultaneously. If two or more of the LEDs are "on" simultaneously, each source is preferably frequency modulated, or otherwise modulated as desired (e.g., by phase or amplitude modulation) so that software of the microcontroller 174 can analyze each PVD's output signal and separate the components arising from each LED's emission, as described further below. For example, in a currently preferred embodiment, the frequency of each LED or other light source is modulated approximately as follows: f1=1613 Hz, f2=1099 Hz, and f3=676 Hz.

With reference to FIG. 2b, the height H of the exemplary PVD 152 is determined by the vertical beam spreads of the cones emitted by the corresponding LEDs 150, as modified by refraction in the meridional plane 154 by the water or other liquid-filled sample vial 130. As shown in FIG. 2c, the width W of the exemplary PVD 152 is determined by the refraction in the x-y plane of the extreme rays 153 emitted in the LED's forward cone of half-angle η (i.e., half the conventional view-angle of the LED 150).

Preferably, three meridional planes 154 are spaced octagonally (i.e., about 45° apart) around the central axis z of the preferably cylindrical sample vial 130. For simplicity, FIG. 2a shows only two meridional planes 154b and 154c. Preferably, each of the meridional planes 154 contains a plurality of LEDs 150 of different peak wavelengths, and a single PVD 152. Thus, the instrument 100 of the preferred embodiment has nine distinct waveband LEDs 150 and three independent broad-area PVDs 152. As may be recognized by those of ordinary skill in the pertinent art based upon the teachings herein, depending on the measurement application, a greater or lesser number of meridional planes may be used, with a greater or lesser number of LEDs per meridional plane. If the sample vial 130 is scaled up or down in diameter, then the optical design will require s1 and s3 to vary (see FIG. 2b), particularly so that the PVD widths W (see FIG. 2c) can be constrained to avoid the physical overlapping of adjacent PVDs. In theoretical design and tests of the preferred embodiment, where the diameter s2 of the sample vial 130 is about 25.4 mm, it has been found that for LEDs with view angles where 2η is less than or equal to about 24°, the useful dimensions in the system are an "s1" of greater than about 5 mm but less than about 10 mm, an "s3" of about 15 mm, and "W"×"H" equal to about 20×40 mm, which are commonly available PVD dimensions. However, as may be recognized by those of ordinary skill in the pertinent art based upon the teachings herein, any of these dimensions and angles may be changed as desired or otherwise required.

Referring now to FIG. 3, when three meridional planes 154a–c are used in an octagonal configuration, it is useful to use only a triplet of orange, red and NIR LEDs 150a in meridional plane 154a, and only deep green and blue LEDs 150c in meridional plane 154c, so that complementary long-pass and short-pass filters 178 and 176, respectively, are deployed in front of PVDs 152a and 152c, respectively, to reduce stray light in the instrument. Wratten gelatin filters #25 and #47 have been found to be satisfactory in this regard for the long and short filters, respectively. In the preferred embodiment, a doublet of yellow and green LEDs 150b are used in meridional plane 154b.

In the embodiment of FIG. 3, a plurality of oscillators 170a–c are switchably connected to the seven LEDs 150a–c, respectively. Upon activation, a power cell 121 provides current to the oscillators. Preferably, each oscillator 170 generates a square wave of a unique frequency. Switching circuitry within a switching circuitry area 172 receives the oscillator outputs and determines which LEDs are illuminated depending upon the specific analysis requested by the user, as will be described in more detail below. For exemplary purposes, a simplified switching scheme is illustrated within the switching circuitry area 172. It will be appreciated by those skilled in the electronic switching art that the specific switching circuitry is not limited to the simplified version illustrated, and that a multitude of combinations beyond that shown are contemplated hereby. The use of electronic switching as opposed to manual allows for rapid sequential readings which are only limited by the settling times of the associated preamplifiers 180a–c, amplifiers 188a–c and display 112. A microcontroller 174 provides the instructions to actuate the oscillators and associated switching circuitry. The microcontroller 174 has a microprocessor 184 and memory 186 operatively connected thereto. It will be appreciated by those skilled in the pertinent art that the microprocessor 174 can directly generate the modulating frequencies for the LEDs 150. Thus, the analog oscillators 170 may be unnecessary.

Still referring to FIG. 3, the seven LEDs 150 are of various colors. Preferably, the seven LEDs consist of light blue (B+) and dark blue (B−) LEDs 150c within the meridional plane 154c, yellow (Y) and green (G) LEDs 150b within the meridional plane 154b, and red (R), orange(O) and infrared (IR) LEDs 150a within the meridional plane 154a. The light emitting from the LEDs 150 passes through the sample vial 130. Within the sample vial 130, the light is refracted and scattered, if turbidity exists, as described above with respect to FIG. 2a, 2b and 2c. It is envisioned that two of the PVDs 152 will receive filtered light. In a preferred embodiment, and as described above, PVD 152a in meridional plane 154c has a red light blocking filter 176 associated therewith (e.g., Wratten #47). and PVD 152a has a blue-green blocking filter 178 associated therewith (e.g., Wratten #25). The use of optical filters aids in reliably separating the average fluorescence emission intensity from scattered intensities. In the case of sensing fluorescence by pulsed excitation or time-delay gated methods, the physical filters may be omitted.

When the PVDs 152a–c convert the light into an electrical signal, the resulting electrical signals are modulated at the same frequencies as that of the oscillators 170a–c which supplied power to the corresponding LEDs 150a–c. The modulation not only allows sorting out the signal from ambient light, which automatically eliminates sun and room lighting from having any effect on the instrument's performance, but also sorts out the signal as opposed to that generated by the other LEDs if more than one LED is activated at any one time.

In a preferred embodiment, one of a plurality of preamplifiers 180a–c boosts each signal generated by the corresponding PVDs 152a–c. The microcontroller 174 determines the timing and duration of the activation of the preamplifiers 180a–c by controlling additional switching circuitry within switching area 182 of a type known to those of ordinary skill in the pertinent art. The boosted signals are variably routed by switching circuitry 182 to a summing amplifier 184 according to the specific analysis requested by the user, as will be described in more detail below. Whichever preamplifiers 180a–c are turned on, the corresponding signal is sent to the summing amplifier 184. The plurality of amplifiers 188a–c are each tuned to a respective frequency of modulation to receive the boosted signals. The tuned amplifiers 188a–c further boost the portions of the signals which are at the modulation frequencies of the oscillators 170a–c while rejecting or dampening other frequencies. The outputs of the tuned amplifiers 188a–c are processed by the microcontroller 174 and input to the display 112 for review by the user. It is envisioned that the display 112 may be a LCD screen, a printout, a digital meter, an analog needle gauge, or the like as is known to those skilled in the art. The outputs of the tuned amplifiers 188a–c also are stored in memory 186 as data. Software stored in the memory 186 provides instructions to the microprocessor 184 to process the data of the particular test. Preferably, the data and/or results are transmitted to an external computer (not shown) via the port 118 for further analysis and long-term storage on a periodic basis. In another embodiment, the above sequence of preamplification, switching, summing and frequency-selective tuned amplification, relevant to the analog representation of the instrument 100 can be replaced at any point after preamplification by a number of alternative digital methods of signal processing. For example, a switched capacitor filter, a digital software filter, synchronous demodulation and the like can be used to extract the signal directly from the PVD preamplifier outputs 180a–c. The flexibility of microprocessor-controlled switching allows measurements of any PVD output caused by any LED's modulated emission.

Figure 4:
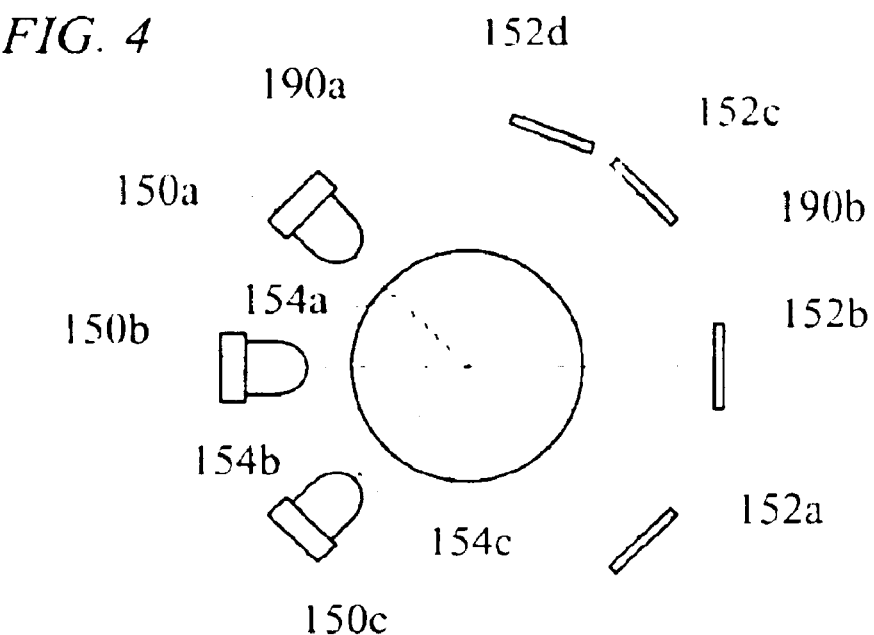
FIG. 4 is a partial schematic, top view of the optics of an instrument constructed in accordance with a preferred embodiment of the subject disclosure.

Referring now to FIG. 4, for simplicity, an overhead plan view of the optical components in another preferred embodiment of the instrument 100 includes three LEDs 150a–c and three PVDs 152a–c in six of the eight positions allowed by an octagonal configuration. The PVDs 152 measure sample transmission in their respective meridional planes 154a–c and, by suitable switching, the light scattered by a turbid liquid, i.e., turbidity. An optional fourth PVD 152d is positioned approximately 22.5 degrees from PVD 152a. The fourth PVD 152d allows for additional collection of light which has been scattered within the sample vial 130. In this embodiment, the protective color filters in meridional planes 154a and 154c have been dispensed with so as to allow scattering measurements from any of the plural LEDs in any meridional plane 154a–c to any of the four PVDs 150a–d. It is envisioned that a multitude of configurations would accomplish the measurements contemplated herein, as would be readily recognized by one skilled in the art upon review of the subject disclosure.

To increase the accuracy of the instrument 100 when post-preamplification and modulated signal measurements are carried out by any desired combination of digitized or analog components, stray light is preferably minimized. Undesirable stray light originates from weak radiation directed from an LED 150 outside the view-angle cone, surface reflection upon entering the sample vial 130, optical scattering by bubbles and/or particulates in the liquid or fluid in the sample vial 130, internal reflection upon exiting the sample vial 130, and/or reflection and scattering at the PVD 152 surface. One advantage of using LEDs in three meridional planes, as shown in the arrangement of FIG. 3, is the reduction of stray light effects. The stray light can be further reduced by the addition of black absorbers 190a and 190b, as shown by broken lines in FIG. 4, within the empty spaces of the unused meridional plane between the LED and PVD sides of the optical system. As shown, the black absorbers between adjacent LEDs can extend inwards substantially adjacent to the sample vial 130.

To further increase the accuracy of the instrument 100, periodic calibration is appropriate. For periodic calibration, the sample vial 130 is sealed and contains pure bubble-free water ("the zeroing bottle"). The zeroing bottle is inserted in the instrument 100 to check and reset in memory 186 the instrument's clean-water transmission and any direct or scattered stray light levels. Resetting the stored base-line levels at the time and location of use corrects for instrument ambient operating temperature fluctuations, component aging, and will signal the user if some mis-function or major departure from factory-set levels has occurred. The clean-water scattered stray light values stored in memory 186 are mathematically subtracted from sample turbidity measurements to determine actual turbidity. Similarly, the clean-water transmission signals stored in the memory 186 for each LED are used as the divisors in computing the transmissivity of the test fluid in the sample vial 130.

Operation

Generally, in operation, the instrument 100 is loaded with standard calibration data. In another embodiment, the instrument 100 performs a series of laboratory readings to generate unique calibration data for storage. It is also envisioned that the instrument may not require stored calibration data, and that field generated reference data will be sufficient to perform the desired analysis. During use of the instrument 100, a user inserts a sample vial 130 into recess 116. As appropriate for a particular analysis, one sample vial 130 may contain clear bubble-free water for zeroing during periodic calibration and other sample vials 130 may contain an unmodified field sample, or a field sample with a reagent added thereto, wherein several readings based upon different substances may be required to complete a particular analysis. The user selects the desired analysis and initiates the process via keypad 114. The microcontroller 174 activates the required LEDs 150a–c and PVDs 152a–c, and provides instruction to the user via display 112 as required for the selected analysis. If necessary, the user manually inserts the appropriately filled sample vial 130 at the appropriate time as prompted by the display 112. The electronics, including without limitation the amplifiers and microcontroller, process the signals generated by the readings, display the results to the user on display 112, and store the results in memory 186 for subsequent download to an external apparatus via port 118. If the instrument 100 becomes low on power, the user may recharge the internal battery via receptacle 120 as would be known to those skilled in the pertinent art.

Color Change Measurements

Referring again to FIGS. 3 and 4, optical absorption of light passing straight-through the sample vial 130 provides color-change data. It is recognized that color is a psycho-physical perception, and therefore an opto-electronic device cannot obtain such a measurement. However, for simplicity, the term color is used to refer to the multi-wavelength photometry disclosed herein. Thus, there is no true concern for the visual color of the fluid target, just the photometric transmission at particular wavelengths.

To obtain a baseline for the instrument 100, precision spectroscopy is conducted in a laboratory. The results are stored in the memory 186 to be used in combination with digitized data from the output of the tuned amplifiers 180a–c (see FIG. 3). Preferably, if a reagent is required to effect the color change, the instrument 100 is carried with a kit containing the various necessary chemicals and reagents.

If a reagent needs to be added to the sample in order to effect a color change, it is envisioned that two samples will be taken. One of the samples will provide a baseline "natural color" reference and the second sample will have the reagent added thereto. Each sample should be measured following substantially the exact same process, but for the addition of the reagent. It is also envisioned that a reagent may need to be added to create a fluorescent effect.

For many color measurements, only red, green and blue+ LEDs 150 need to be utilized. In one embodiment, the red, green and blue+LEDs are LEDs 150a–c, respectively, as shown in FIG. 4. The three LEDs are each modulated at a different frequency. As a result of the three beams of light passing through the sample vial 130, red, blue+and green readings are output to the display 112 indicating a color reading for the sample. For less sophisticated color tests, the redundancy of three different color channels may not be necessary. For example, a bluish sample may only require color analysis using the red channel. For more sophisticated color tests, any subset of up to twelve different color LEDs, e.g., as in an octagonal configuration, operated simultaneously at different modulation frequencies, or sequentially at a single modulation frequency, may be used for a color analysis.

In another embodiment, the instrument 100 indicates the concentration of a predetermined impurity. The concentration is based upon comparison of data from a field sample to data points stored in the memory 186. In the preferred embodiment, the stored data is representative of a log-linear Beer's Law plot. A Beer's Law plot is made by measuring the transmitted light signal (T) of solutions of varying concentration without varying the path length of the light or the wavelength, and dividing T by the transmitted light signal of a pure water sample ($T_o$) with the same path length and wavelength. A plot of the logarithm of the ratio against concentration is a Beer's Law plot. A linear Beer's Law plot indicates that the Beer-Lambert relationship holds for the solution at the particular wavelength and the Beer's Law plot is used in determining the concentration of unknown solutions. Symbolically, the Beer-Lambert relationship is "$T/T_o=10^{-A}$", in which case "$A=\epsilon bc$", where A is the absorption coefficient, $\epsilon$ is the molar absorbtivity, b is the path length, and c is the concentration of the compound in the solution. Preferably, the stored data points are generated under controlled conditions in a laboratory by measuring several samples of known impurity concentrations with the instrument 100. Upon acquisition of an absorption or transmission reading from a field sample, the stored data is compared to the reading from the field sample to find the corresponding impurity concentration in a manner known to those of ordinary skill in the pertinent art based upon review of the teachings disclosed herein. For example, the microcontroller 174 selects first and second data points above and below, respectively, the reading from the field sample. Based upon the field sample reading, and the first and second data points, the microcontroller mathematically interpolates to arrive at an impurity level for the field sample.

It also will be appreciated by those skilled in the art that if the natural color of the field sample has undesirable turbidity or coloration, a natural color sample may be used as a zeroing reference point to further enhance the accuracy of the resulting concentration analysis. In another embodiment, to further increase the reliability of the concentration analysis, multiple colors may be utilized with corresponding sets of stored data points. Thus, the results for analysis with one color would verify the results of another color.

Scattering and Turbidity Measurements

Figure 5:
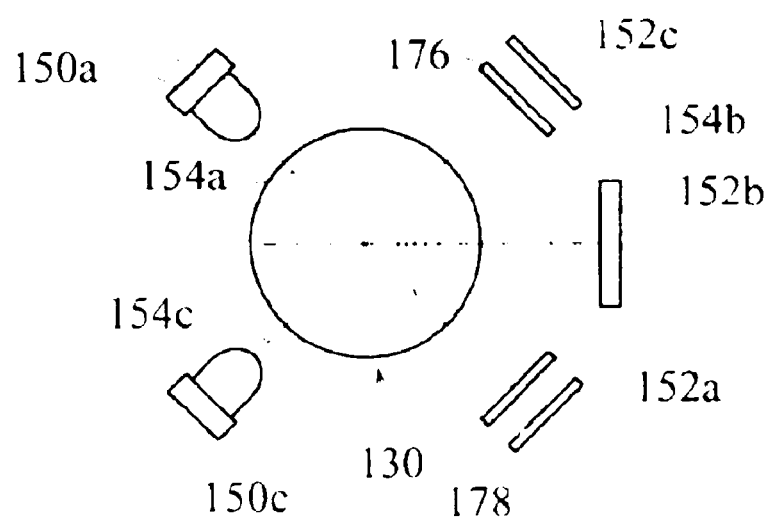
FIG. 5 is a partial schematic, top view of the optics used for a scattering measurement in accordance with a preferred embodiment of the subject disclosure.

FIG. 5 depicts a currently preferred configuration of the components for conducting turbidity measurements, and is seen to contain a portion of the same components in the same relative positions as shown in FIGS. 3 and 4. The switching circuitry changes according to microprocessor control to accomplish the selected turbidity measurement in a manner known to those of ordinary skill in the pertinent art based upon the teachings herein. Turbidity data is preferably based upon 45° light scattering at about 45° or thereabouts.

In one embodiment, blue turbidity is measured by activating the blue+beam's LED 150c. It will be appreciated by those skilled in the art that such an instrument 100 may contain additional components which are not shown for simplicity. For example, such components would process the signals and facilitate performing additional measurements as described hereinbelow. As light from the blue+LED 150c passes through the sample vial 130, a portion of the light is scattered and impinges upon PVD 152b of the adjacent channel. PVD 152b has no color filter so a signal modulated at the frequency of blue light is generated by the scattering. The amplifier 188 (see FIG. 3) is tuned to the blue light frequency. After first measuring the sample transmission by amplifying the signal from PVD 152a, the amplifier 188 is then switched to amplify the signal of PVD 150b only, and the strength of the signal is proportionate to the 45° turbidity. As a result, the instrument 100 displays a value on the display 112 indicative of the turbidity of the sample.

Still referring to FIG. 5, NIR emission turbidity can also be measured. Preferably, LED 150a is a modulated source providing NIR, PVD 152a is the transmission monitor, and unfiltered PVD 152b is the sensor for NIR scattering approximately 45° off-axis. Since international practices in monitoring water turbidity currently specify the use of 860 nm NIR light in some instances, and long-wave blue light in others, the ability to measure both turbidities in the same instrument 100, with no moving parts, is easy for the user and avoids potential operator error. In still another embodiment, as shown in FIG. 4, placement of a fourth and/or a fifth PVD (not shown) can receive 22.5° light from meridional planes 154a and c, respectively, for a corresponding turbidity measurement.

For measurements, and particularly for turbidity, zeroing technique and cleanliness are important because air bubbles, lint, smudges and the like may cause undue scattering which may in turn affect the results. In a preferred embodiment, a technician follows the method below in order to efficiently and accurately conduct a turbidity measurement:

1. Select turbidity from a list of measurements shown on the display 112 via the keypad 114.
2. Perform a periodic zeroing to acquire and store clean-water transmissions and stray light signals for all components to be used in the specific turbidity test. As necessary, cleaning and wiping of sample vial 130 is performed. Additionally, inspect for potential sources of undesirable turbidity such as, without limitation, minute air bubbles clinging to the inner glass and/or water interface of the chamber.
3. Fill a sample vial 130 with a sample of the water to be measured. Inspect the filled sample vial 130 for potential sources of undesirable turbidity similar to the previous step.
4. Insert the sample vial 130 into the instrument 100.
5. Initiate the measurement by depressing an appropriate button on the keypad 114 and view the desired result on the display 112.

If addition of a reagent is required to create the scattering of particles within the sample, additional steps may be required. An additional sample vial 130 should be filled with a sample and sealed. Even though no reagent is added, the additional sample vial 130 should be treated, i.e., shaken, substantially exactly as the sample vial 130 with the reagent, and a baseline reading taken to account for any natural turbidity present in the original sample. Thus, by using such a reference point with a similar shaking history, the effects of settling and preparation within the sample are mathematically subtracted by the microcontroller 174, in a manner known to those of ordinary skill in the pertinent art, to yield a true turbidity result.

Fluorescence Measurements

Still referring to FIG. 5, fluorescence can be measured using direct and approximately 90° emission. In one embodiment, excitation occurs along the blue channel by LED 150c. The meridional PVD 152c indicates blue LED intensity when the sample vial 130 contains clear water, natural liquid transmittance when the sample chamber contains a "natural color" water sample, and reacted liquid transmittance when the sample vial 130 contains the natural water after chemical reaction with a fluorogenic agent. When a fluorescent reaction product emits in the red, the signal generated by PVD 152c is solely that of the blue exciting light transmitted through the sample vial 130 because the red light is blocked by the filter 176 located in front of PVD 152c. The red fluorescence is detected by PVD 152a at about 90° to the exciting blue light beam because the red fluorescence passes through the filter 178 located in front of PVD 152a. Preferably, during this measurement, all LEDs in the instrument except the blue+LED 150c are switched off to reduce the signal-to-noise ratio. The red fluorescence signal arising from PVD 152a has the same modulation frequency as that of the exciting beam, and therefore to still further reduce electronic noise, the signal from direct PVD 152c is switched off when that from PVD 152a is measured. It will be recognized by those of ordinary skill in the art that the instrument 100 for fluorescence measurement is physically no different from the embodiments discussed above for transmittance and turbidity measurements, and that only electrical switching changes controlled by the software of the microprocessor 184 in a manner known to those of ordinary skill in the pertinent art are required.

In another embodiment, multiple blue LEDs on the meridional plane 154c increase excitation intensity, and in turn increase the generated signal strength. To further increase the strength of the fluorescence signal, receiving PVD 152a may be placed closer to the sample vial 130 to increase the collected fluorescence signal. The fluorescence sensitivity can be increased still further if the receiving PVD 152a is an appropriately molded Winston cone and avalanche photodiode detector, as would be appreciated by those of ordinary skill in the pertinent art.

Multivariate Measurements

Multivariate analysis is analyzing two or more different sets of data simultaneously using matrix mathematics in a manner known to those of ordinary skill in the pertinent art to separate out the results. For example, turbidity and fluorescence measurements can be collected simultaneously with the instrument 100. Simultaneous transmission and scattering measurements can be taken with no cross-talk because the LEDs 150 are modulated at different frequencies. Simultaneous transmission measurements at multiple wavelengths can be made on a liquid sample undergoing multiple, non-interacting chemical tests which produce known optical absorption changes at different wavelengths. Various algorithms of a type known to those of ordinary skill in the pertinent art are carried out by the microcontroller 174 to process such multivariate data. Examples of multivariate analysis are given in "Applications and Limitations of Genetic Algorithms for the Optimization of Multivariate Calibration Techniques" by Matthew Mosley (Clemson University, 1998), which is incorporated herein by reference in its entirety.

A plurality of readings can also be conducted sequentially. The intervals between readings are limited by the settling time of the amplifiers and the display 112. For example, photometric and fluorometric, or photometric and turbidimetric measurements can be conducted within seconds by multiple light beams directed along multiple meridional planes 154 of the sample vial 130. While such sets of sequential measurements require only conventional calculational means, the intentional redundancy of data supplied is advantageously treated by multivariate methods known to those of ordinary skill in the pertinent art to greatly increase the user's confidence in, and awareness of, the statistical accuracy of the instrument's output.

Alternative Embodiments

Figure 6A:
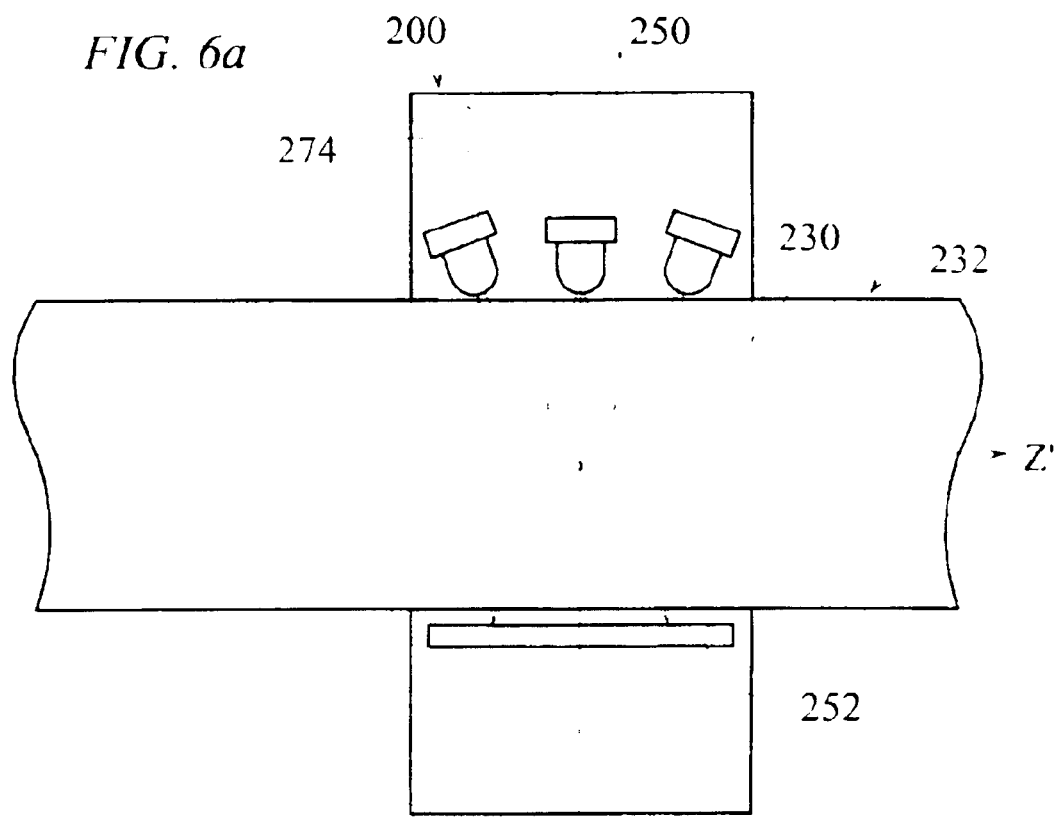
FIG. 6a illustrates a perspective view of another instrument for measuring optical transmission, turbidity and fluorescence of a fluid sample flowing in a transparent conduit in accordance with the subject disclosure.
Figure 6B:
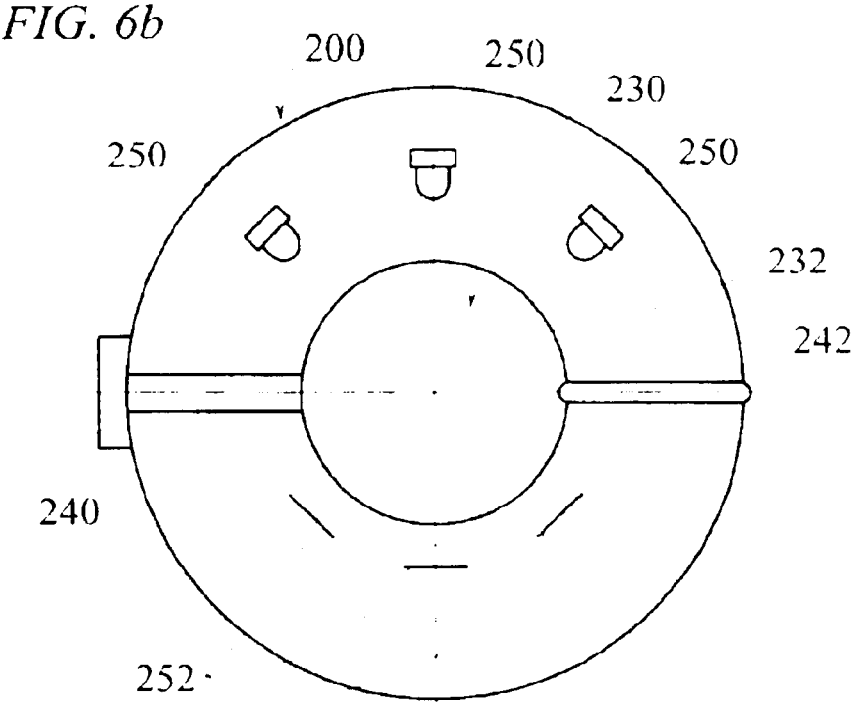

Referring to FIGS. 6a and 6b, the instrument 200 is adapted to take measurements of a fluid or other material passing through the sample chamber 230 in the form of a transparent or translucent conduit 232. To achieve this, the instrument 200 contains multiple LEDs 250 and multiple PVDs 252 on multiple meridional planes (only one shown for simplicity). A microcontroller 274 is also housed within the instrument 200. Preferably, the LEDs 250 are secured on one side of the conduit 230 and the PVDs 252 on the other side. For simplicity, only one set of LEDs 250 and PVD 252 are shown in FIG. 6a. The instrument 200 is halved along a center line passing parallel to the sample chamber axis z'. Preferably, the two halves of the instrument 200 are secured together by a hinge 240 and a closing latch 242. The transparent conduit 230 defines the sample chamber therein. In one embodiment, the outer diameter of the conduit 230 is about 1 inch to allow a configuration of meridional planes 254 as described above. Such an arrangement permits continuous transmission, turbidity and fluorescence measurements of a material flowing through the conduit 230. It is envisioned that this arrangement is applicable in industrial photochemical and biochemical reactors, municipal water and sewerage plants, nuclear power plant fuel rod storage facilities, and the like.

In monitoring flowing fluids, it may be advantageous to scale down the optical sensing instrument 200 to accept sample pipe outer diameters of 0.5 inches or less. Accordingly, in the scaled-down embodiment, the LEDs should be 3 mm instead of 5 mm with small view angles of approximately 20°. Alternatively, semiconductor lasers could be used as the radiation source where appropriate in lieu of the LEDs 250, with PVDs 252 of even smaller surface area than 20×20 mm as described above. Applications utilizing 0.5 inch diameter quartz pipe sample chambers include everything mentioned above, plus common relatively smaller tube piping in chemical, pharmaceutical and food processing plants and the like. As may be recognized by those of ordinary skill in the pertinent art based on the teachings herein, the optical components of the instrument 200 may be scaled up or down to meet the requirements of any of numerous different applications or uses that are currently or later become known.

Only minor design changes in the positioning of the PVDs 252 along the axes of their meridional planes 254 are required to accommodate monitoring of petrochemical fluids having refractive indices higher than water, e.g., in the 1.4–1.5 range. Transmission and particulate concentration monitoring can also be carried out on low refractive index fluids, such as flowing industrial and engine exhaust gases, and low-temperature super-critical and critical fluids, such as condensed $CO_2$. In order to collect substantially all of the light energy, these measurements require the use of large-area PVDs and very low view-angle LEDs, such as 10° light cones and/or semiconductor lasers, because no appreciable refractive light-beam shaping takes place in passage through the sample. Preferably, for high temperature and low temperature flowing fluids, the sample-containing tubes 230 are vacuum sealed inside somewhat larger outer quartz tubes to thermally insulate the samples from the optical sensing instrument 200. In such an arrangement, the PVDs 252 are preferably designed to fit closely around the outer insulating tube.

Figure 7A:
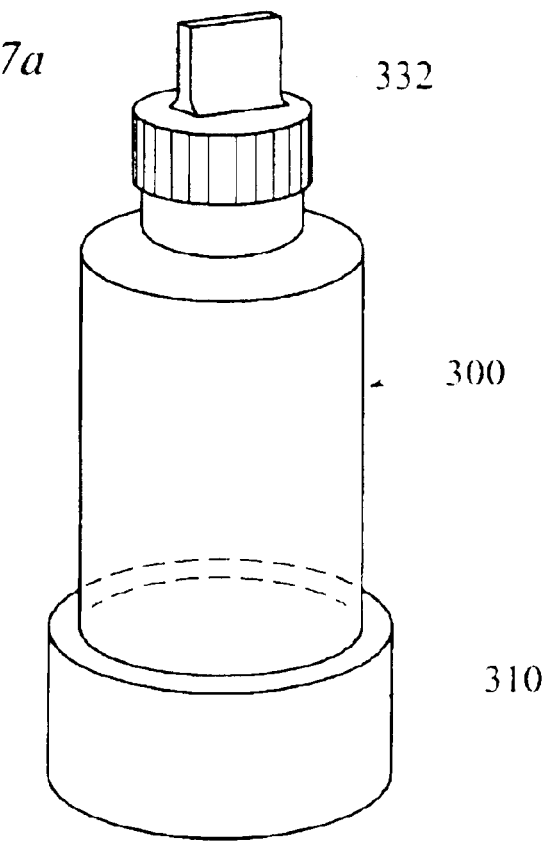
FIG. 7a is a perspective view of a sample vial in accordance with an additional preferred embodiment of the subject disclosure.
Figure 7B:
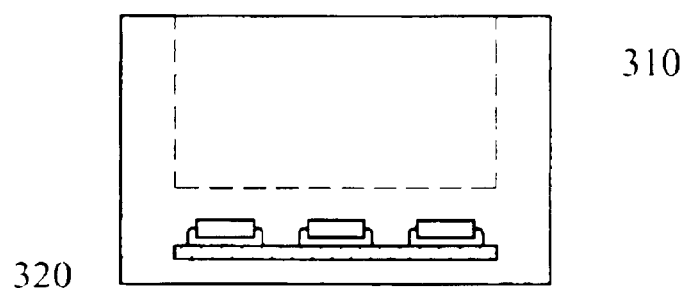
Figure 7C:
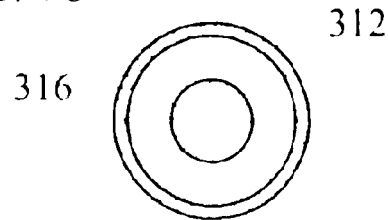

Referring now to FIGS. 7a through 7c, another preferred embodiment makes use of a sample chamber 300 with an integrated circuit 320. The sample chamber 300 has a cap 332 and a plastic base 310. The base 310 is secured by a press fit, epoxy or other method known to those of ordinary skill in the pertinent art. As shown in FIG. 7b, the base 310 contains an embedded integrated circuit or printed circuit board 320 which carries electronic devices such as non-volatile, erasable, writable memory. The electronic devices store specific test software instructions, test-specific calibration data, user interface configuration data and the like as may be desired. The printed circuit board 320 of the sample vial 300 also contains an identifying number which positively relates the sample vial 300 to prepackaged chemicals, such as reagents, that may be inside or supplied with the sample vial 300. Upon insertion in the instrument 100, the instrument 100 recognizes the sample chamber 300 by the identifying number, and receives the necessary instructions to perform the appropriate measurements and to automatically start the selected test. Thus, the user only needs to fill the sample chamber within the sample vial 300 and insert the sample vial 300 in the instrument 100. If desired, the sample chamber 300 may be reusable depending upon the chemical test or series of tests conducted therewith.

Referring to FIG. 7c, the sample vial 300 communicates with the instrument 100 through the base 310, when placed in the recess 116 of the instrument 100. Preferably, the weight of the filled sample vial 300, regardless of its rotational orientation in the recess 116, causes contacts in the base 310 to come into electrical contact with spring-loaded contact buttons embedded in the recess 116 of the instrument 100. In one embodiment, an outer contact ring 312 mounted within the recess 116 of the instrument establishes the common electrical ground, and a central contact 316, also mounted on the base of the recess 116 and electrically coupled to the microprocessor 184, communicates power and multiplexed electrical signals back and forth. It is also envisioned that the base 310 and instrument 100 may be electronically connected by a capacitive coupling, by low-power "RFID"-type technology, by magnetic coupling, by any ordinary opto-electronic remote control, and the like.

It will be appreciated by those of ordinary skill in the pertinent art that the components and dimensions described above are only exemplary and can be changed as desired or required by new applications. Accordingly, the detailed description of preferred embodiments is to be taken in an illustrative, as opposed to a limiting sense. While the invention has been described with respect to preferred embodiments, those skilled in the art will readily appreciate that various changes and/or modifications can be made to the invention without departing from the spirit or scope of the invention as defined by the appended claims.

What is claimed is:

1. A device for optically measuring qualities of a substance in ambient light comprising:
    at least one translucent wall defining a sample chamber for receiving therein the substance to be measured and defining an axis;
    a first channel defining a first meridional plane and including thereon:
        at least one radiation source mounted adjacent to the sample chamber, wherein the at least one radiation source includes a first radiation source and a second radiation source, the first radiation source and the second radiation source being axially spaced relative to each other, the first radiation source emits a modulated beam of radiation distinguishable from the ambient light based on said modulation and the second radiation source emits a modulated beam of radiation distinguishable from the ambient light based on said modulation; and
        at least one detector angularly spaced about the axis of the sample chamber relative to the first and second radiation sources, wherein the at least one detector includes a first detector, the first radiation source is positioned so that a principle ray emitting therefrom substantially passes onto the first detector, the second radiation source is positioned so that a principle ray emitting therefrom substantially passes onto the first detector, the first detector receives the modulated beams of radiation after passage through the sample chamber and substance to be measured therein, and generates a modulated output signal indicative of the intensity of the radiation of the beams impinging thereon;
    a second channel defining a second meridional plane and including thereon:
        at least one radiation source mounted adjacent to the sample chamber, wherein the at least one radiation source of the second channel includes a third radiation source that emits a modulated beam of radiation distinguishable hum the ambient light based on said modulation; and
        at least one detector annularly spaced about the axis of the sample chamber relative to the third radiation source, wherein the at least one detector of the second channel receives the modulated beam of radiation emitted by the third radiation source after passage through the sample chamber and substance to be measured therein, and generates a modulated output signal indicative of the intensity of the radiation of the beam of the third radiation source impinging thereon;
    a controller coupled to the first radiation source and the first detector for activating the first radiation solute and processing the output signal of the first detector; and
    a display coupled to the controller.

2. A device as recited in claim 1, further comprising a housing defining a recess, and wherein the at least one translucent wall is formed by a vial defining the sample chamber therein, and the first radiation source and first detector are mounted adjacent to the recess.

3. A device as recited in claim 1, wherein the at least one translucent wall is approximately cylindrical.

4. A device as recited in claim 1, further comprising at least one oscillator coupled to the at least one radiation source of the first channel for modulating the at least one radiation source of the first channel.

5. A device as recited in claim 1, further comprising at least one amplifier coupled to the first detector for boosting the output signal and dampening other frequencies.

6. A device as recited in claim 1, wherein said at least one radiation source of the second channel is angularly spaced about the axis of the chamber relative to the first radiation source.

7. A device as recited in claim 1, wherein the display comprises a display for displaying measurement reading based on the modulated output signals.

8. A device as recited in claim 1, further comprising an optical longpass filter positioned in front of the at least one detector of the second channel for separating a fluorescence emission intensity from scattered intensities of the at least one radiation source of the first channel and for reducing stray light.

9. A device as recited in claim 1, wherein the principle ray of the first radiation source and the principle ray of the second radiation source each extend through the axis onto a central region of the first detector.

10. A device as recited in claim 1, wherein the first and second radiation sources each comprise a light emitting diode.

11. A device as recited in claim 1, wherein the at least one translucent wall defining the sample chamber comprises at least one optically refractive wall and wherein the at least one optically refractive wall has a refractive power adapted to focus said modulated beam of radiation emitted from said first radiation source and said modulated beam of radiation emitted from said second radiation source onto said first detector.

12. A device as recited in claim 11, further comprising a vial defining therein the sample chamber and a recess for removably receiving therein the vial.

13. A device as recited in claim 11, wherein the substance comprises a field sample, the sample chamber is defined by a conduit allowing the field sample to flow therethrough, the field sample has a concentration of an impurity, and the controller further operative to monitor the concentration of the impurity.

14. A device as recited in claim 1, wherein the display comprises a display for generating a human readable measurement reading.

15. A device as recited in claim 1, wherein the modulated beam of the first radiation source is modulated at a first modulation frequency and the modulated beam of the second radiation source is modulated at a second modulation frequency different than the first modulation frequency.

16. A device as recited in claim 15, wherein the modulated beam of the third radiation source is modulated at a third modulation frequency different than the first modulation frequency and the second modulation frequency.

17. A device as recited in claim 1, further comprising:
data including a plurality of reference measurements based upon a plurality of different reference samples, each reference sample having a different concentration of an impurity, and
wherein the controller comprises a controller for (i) automatically comparing the modulated output signal from the first detector to at least a portion of the plurality of reference measurements to determine a concentration of an impurity in the substance and (ii) generating an output signal indicative of the concentration of the impurity in the substance.

18. A device for analyzing radiant transmission and scattering of an longated sample, wherein the elongated sample defines art axis, the device comprising:
a first channel defining a first meridional plane having the axis extending therethrough and including thereon at least one radiation source mounted adjacent to the sample, the at least one radiation source including a first radiation source for emitting a first beam of radiation through the sample and a second radiation source for emitting a second beam of radiation through the sample, the first radiation source and the second radiation source being axially spaced relative to each other, and at least one sensor angularly spaced about the axis of the sample relative to the first radiation source for generating a first output signal indicative of the intensity radiation impinging thereon, the at least one sensor including at first sensor for detecting radiation impinging thereon, the first radiation source being positioned so that a principle ray emitting therefrom substantially passes onto the first sensor, the second radiation source being positioned so that a principle ray emitting therefrom substantially passes onto the first sensor; and
a second channel defining a second meridional plane having the axis extending therethrough and including thereon at least one radiation source mounted adjacent to the sample, the at least one radiation source of the second channel including a third radiation source for emitting a third beam of radiation through the sample, and at least one second sensor angularly spaced about the axis of the sample relative to the third radiation source for generating a second output signal indicative of the intensity of radiation impinging thereon.

19. A device as recited in claim 18, wherein the first radiation source and the second radiation source each includes a light emitting diode positioned so that a principle ray emitting therefrom substantially passes through the axis of the sample and onto the first sensor.

20. A device as recited in claim 18, wherein the first and third radiation sources are selected from the group including green, red, yellow, orange, blue and nearinfrared light emitting diodes.

21. A device as recited in claim 18, wherein the first and second channels are angularly spaced approximately 45° apart.

22. A device as recited in claim 18, further comprising a third channel defining a third meridional plane extending through the axis and including thereon at least one radiation source mounted adjacent to the sample, the at least one radiation source of the third channel including a fourth radiation source for emitting a fourth beam of radiation through the sample, and at least one third sensor angularly spaced about the axis of the sample relative to the fourth radiation source for generating a third output signal indicative of the intensity of radiation impinging thereon.

23. A device as recited in claim 18, wherein the second and third channels are angularly spaced approximately 45° apart and the first and third channels are angularly spaced approximately 90° apart.

24. A device as recited in claim 22, further comprising a fourth channel defining a fourth meridional plane extending through the axis and including thereon at least one radiation source mounted adjacent to the sample, the at least one radiation source of the fourth channel including a fifth radiation source for emitting a fifth beam of radiation through the sample, and at least one fourth sensor angularly spaced about the axis of the sample relative to the fifth radiation source for generating a fourth output signal indicative of the intensity of radiation impinging thereon.

25. A device as recited in claim 24, wherein the first and fourth channels are angularly spaced approximately 22.5° apart.

26. A device as recited in claim 18, wherein the axis lies within the first meridional plane.

27. A device as recited in claim 26, wherein the axis lies within the second meridional plane.

28. A device as recited in claim 18, further comprising a translucent cell for receiving the sample; and wherein the translucent cell defines an optically refractive element adapted to focusing the first beam of radiation on the first detector.

29. A device as recited in claim 28, wherein the first radiation source comprises a light source for emitting a cone of light and the translucent cell defines the only refractory element disposed along a light path between the first radiation source and the first sensor.

30. A device as recited in claim 29, further comprising:
a controller coupled to the first sensor; and
a display for converting an output of the controller into a human readable form.

31. A device as recited in claim 28, wherein the first radiation source comprises a light emitting diode.

32. A device as recited in claim 18 further comprising electronics for activating each of the channels and processing the first and second output signals generated thereby.

33. A device as recited in claim 18, wherein the at least one sensor of the first channel further detects radiation that is emitted from the at least one radiation source of the second channel and scattered through the sample.

34. A device as recited in claim 28, wherein the translucent cell is a conduit for receiving the sample therethrough.

35. A device as recited in claim 28, further comprising a beam-splitter positioned in front of the first radiation source for directing a portion of the first beam of radiation and for indicating an output power of the first radiation source to thereby monitor performance of the first radiation source.

36. A device as recited in claim 28, further comprising an amplifier operatively associated with the at least one sensor of the first channel for boosting the first output signal of the at least one sensor of the first channel.

37. A device as recited in claim 28, further comprising an oscillator operatively associated with the first radiation source for modulation the first beam of the first radiation source at a first modulated frequency.

38. A device as recited in claim 28, further comprising a reagent contained within the translucent cell for mixing with the sample and creating particles which scatter the light.

39. A device as recited in claim 28, further comprising a reagent contained within the translucent cell for mixing with the sample and creating fluorescence.

40. A device as recited in claim 28, further comprising a reagent contained within the translucent cell for mixing with the sample and creating an optical absorption hand which reduces a transmissivity of the material.

41. A device as recited in claim 28, further comprising a controller operatively coupled to the first radiation source and first sensor, and wherein the translucent cell includes an electrical circuit mounted thereon and operatively associated with the controller to provide instructions for use in analyzing the radiant transmission and scattering of the sample.

42. A device as recited in claim 28, wherein the translucent cell includes a cap attachable thereto for sealing the sample within the cell.

43. A device as recited in claim 18, further comprising:
(a) a housing defining a recess for receiving a sample chamber that has at least one memory and is adapted to receive the sample; and
(b) at least one processor to communicate with the at least one memory.

44. A device as recited in claim 43, wherein the first radiation source is a light emitting diode.

45. A device as recited in claim 43, wherein the first sensor is a photovoltaic detector.

46. A device as recited in claim 43, further comprising:
at least one oscillator within the housing and operatively connected to the first radiation source; and
a power cell within the housing for driving the at least one oscillator.

47. A device as recited in claim 46, further comprising said sample chamber and wherein said sample chamber further includes a base having a printed circuit board that supports the at least one memory.

48. A device for optically measuring qualities of a substance in ambient light comprising:
first means defining a sample chamber for receiving therein the substance to be measured and defining an axis;
a first channel defining a first meridional plane and including thereon:
second means mounted adjacent to the sample chamber for emitting a modulated beam of radiation distinguishable from the ambient light based on said modulation;
third means mounted adjacent to the sample chamber for emitting a modulated beam of radiation distinguishable from the ambient light and the modulated beam of the second means based on said modulation, the second means and the third means being axially spaced relative to each other; and
fourth means angularly spaced about the axis of the sample chamber relative to the second means for receiving the modulated beam of radiation of the second means after passage through the sample chamber and substance to be measured therein, and for generating a modulated output signal indicative of the intensity of radiation impinging thereon, wherein the fourth means includes a first detector for detecting radiation, the second means is positioned so that a principle ray emitting therefrom substantially passes onto the first detector, and the third means is positioned so that a principle ray emitting therefrom substantially passes onto the first detector;
a second channel defining a second meridional plane and including thereon:
fifth means mounted adjacent to the sample chamber for emitting a modulated beam of radiation; and
sixth means angularly spaced about the axis of the sample chamber relative to the fifth means for receiving the modulated beam of radiation of the fifth means after passage through the sample chamber and substance to be measured therein, and for generating a modulated output signal indicative of the intensity of radiation impinging thereon; and
seventh means coupled to the second and fourth means for activating the second means and processing the output signal of the fourth means.

49. A device as recited in claim 48, wherein the second means is a radiation source.

50. A device as recited in claim 49, wherein the radiation source is light emitting diode and an oscillator connected thereto.

51. A device as recited in claim 48, wherein the first detector is a photovoltaic sensor.

52. A device as recited in claim 48, wherein the seventh means is a microprocessor and memory operatively connected to the second and fourth means.

53. A device as recited in claim 48, wherein the sample chamber comprises a removable sample chamber for receiving therein a sample of the substance and having at least one memory; and
wherein the seventh means is in communication with the at least one memory.

54. A device as recited in claim 53, wherein the first means comprises a vial.

55. A device as recited in claim 53, wherein the second means comprises a light emitting diode and the first detector comprises a photovoltaic detector.

56. A device as recited in claim 53, wherein the at least one memory comprises random access memory and read only memory.

57. A device an recited in claim 53, wherein the seventh means comprises a microprocessor and a software program.

58. A method for optically measuring qualities of a substance in ambient light comprising the steps of:

providing a sample chamber defining an axis for receiving therein the substance to be measured;

providing a first channel defining a first meridional plane and including thereon at least two radiation sources mounted adjacent to the sample chamber and at least lone detector angularly spaced about the axis of the sample relative to the first radiation source for generating a first output signal indicative of the intensity of radiation impinging thereon, the at least two radiation sources including a first radiation source and a second radiation source, the at least one detector including a first detector, the first and second radiation sources being axially speed relative to each other, the first radiation source being positioned so that a principle ray emitting therefrom substantially passes onto first detector, the second radiation source being positioned so that a principle ray emitting therefrom substantially passes onto the first detector;

emitting modulated beams of radiation from the first and second radiation sources, each of the first and second radiation sources being modulated at a different frequency and, therefore, distinguishable from the ambient light and each other based on said modulation;

providing a second channel defining a second meridional plane and including thereon at least one radiation source mounted adjacent to the sample chamber and at least one detector angularly-spaced about the axis of the sample chamber relative to the at least one radiation source of the second channel;

receiving the modulated beams of radiation by the first detector after passage through the sample chamber and substance to be measured therein;

generating a modulated output signal indicative of the intensity of the radiation of the modulated beams impinging on the first detector;

activating by a controller the first radiation source and the first detector;

processing the modulated output signal; and providing a display for providing measurement readings based on the modulated output signal.

59. A method according to claim 58, wherein any angle effects are automatically taken into account by storing a data point based upon a calibration with a pure water sample.

60. A method according to claim 59, further comprising the step of dampening any signal at the frequency of ambient light.

61. An instrument for analyzing color and scattering of a sample, wherein the sample defines an axis, the instrument comprising:

first means for defining a first meridional plane and including thereon second means for emitting a beam of radiation modulated at a first frequency, the second means mounted adjacent to the sample for emitting said beam of radiation through the sample, third means for emitting a beam of radiation modulated at a second frequency that is different than the first frequency, the third means mounted adjacent to the sample for emitting said beam of radiation through the sample, the second means and the third means being axially spaced relative to each other, and fourth means for sensing angularly spaced about the axis of the sample relative to the second means and including a detector for sensing radiation, the second means being positioned so that a principle ray emitting therefrom substantially passes onto the detector, the third means being positioned so that a principle ray emitting therefrom substantially passes onto detector, the fourth means generating a first output signal indicative of the intensity of radiation impinging thereon;

fifth means for defining a second meridional plane and including thereon sixth means for emitting a beam of radiation, the sixth means mounted adjacent to the sample for emitting said beam of radiation through the sample, and seventh means for sensing angularly spaced about the axis of the sample relative to the sixth means for generating a second output signal indicative of the intensity of radiation impinging thereon; and eighth means for activating the first and fifth means and processing said output signals generated thereby.

62. An instrument as recited in claim 61, wherein the eighth means activates the second and sixth means simultaneously and corresponding signals generated thereby are distinguishable.

* * * * *